United States Patent
Grandy et al.

(10) Patent No.: US 6,280,973 B1
(45) Date of Patent: Aug. 28, 2001

(54) MAMMALIAN METHADONE-SPECIFIC OPIOID RECEPTOR GENE AND USES

(75) Inventors: David K. Grandy; James R. Bunzow, both of Portland, OR (US); Olivier Civelli, Aesch (CH)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 09/510,473

(22) Filed: Feb. 22, 2000

Related U.S. Application Data

(62) Division of application No. 09/170,331, filed on Oct. 13, 1998, now Pat. No. 6,028,175, which is a division of application No. 08/911,245, filed on Aug. 15, 1997, now Pat. No. 5,821,067, which is a division of application No. 08/149,093, filed on Nov. 8, 1993, now Pat. No. 5,658,783.

(51) Int. Cl.$^7$ .......................... C12P 21/06; C07H 21/04; C12N 5/00; C12N 15/74; C12N 1/20
(52) U.S. Cl. ...................... 435/69.1; 435/70.1; 435/71.1; 435/71.2; 435/325; 435/471; 435/252.3; 435/320.1; 536/23.5
(58) Field of Search ................................ 435/69.1, 70.1, 435/71.1, 71.2, 320.1, 325, 471, 252.3; 536/23.5

(56) References Cited

U.S. PATENT DOCUMENTS

| | | |
|---|---|---|
| 5,658,783 | 8/1997 | Grandy et al. . |
| 5,821,067 | 10/1998 | Grandy et al. . |
| 5,985,600 * | 11/1999 | Evans et al. . |
| 6,028,175 | 2/2000 | Grandy et al. . |

OTHER PUBLICATIONS

Gluzman et al., (1981) *Cell*, 23:175–182.
Walters, (1993) "Computer–Assisted Modeling of Drugs." *Pharmaceutical Biotechnology*, pp. 165–174.
Thomas & Capecchi, (1987) *Cell*, 51: 503–512.
Bertling, (1987) *Bioscience Reports*, 7:107–112.
Smithies et al., (1985) *Nature*, 317: 230–234.
Kieffer et al,. (1992) *Proc. Natl. Acad. Sci.*, 89: 12048–12052.
Evans et al., (1992) *Science*, 258: 1952–1955.
Chirgwin et al., (1979) *Biochemistry*, 18: 5294–5299.
Saiki et al., (1988) *Science*, 239:487–491.
Sanger et al., (1977) *Proc. Natl. Acad. Sci.*, 74:5463–5467.
Eisenberg et al., (1984) *J. Molec. Biol.*, 179: 125–142.
Chen & Okayama, (1987) *Molec. Cell. Biol.*, 7: 2745–2752.
Bunzow et al., (1988) *Nature*, 336: 783–787.
Arriza et al., (1988) *Neuron*, 1: 887–900.
Blakely et al., (1991) *Anal. Biochem.*, 194: 302–308.
Felgner et al., (1987) *Proc. Natl. Acad. Sci.*, 84: 7413–7417.
Arriza et al., (1992) *J. Neurosci.*, 12: 4045–4055.
Smith & Johnson, (1988) *Gene*, 67: 31–40.
Chen et al., (1993) "Molecular Cloning and Functional Expression of a ∪–Opioid Receptor from Rat brain." *Molec. Pharmacol.*, 44: 8–12—P.
Yasuda et al., (1993) "Cloning and functional comparison of κ and ζ opioid receptors from mouse brain." *Proc. Natl. Acad. Sci.*, 90: 6736–6740.
Bzdega et al., (1993) "Regional expression and chromosomal location of the ζ opiate receptor gene.", *Proc. Natl. Acad. Sci.*, 90: 9305–9309.
Brownstein et al., (1993) "A brief history of opiates, opioid peptides amid opioid receptors." *Proc. Natl. Acad. Sci.*, 90: 5391–5393.
DiChara & North, (1992) "Neurobiology of opitate abuse." *Trends in Phamacol. Sci.*, 13:185–193.
Maneckjee and Minna, (1992) "Nonconventional opioid binding sites mediate growth inhibijtory effects of methadone on human lung cancer cells." *Proc. Natl. Acad. Sci.*, 89:1169–1173.
McKnight & Rees, (1991) "Opioid Receptors and their Ligands." *Neurotransmissions*, 7: 1–6.
Goldstein, (1987) "Binding selectivity profiles for ligands of multipe receptor types: focus on opiod receptors." *Trends in Pharmacol. Sci.*, 8: 456–459.
Kristensen et al., (1995) *Life Sciences*, vol. 56, p. 56.
Fukuda et al., (1993) *FEBS Letters*, vol. 327, p. 311.
Wang et al., (1993) *PNAS*, vol. 90, p. 10230.
Reeck et al., (1987) *Cell*, vol. 50, p. 667.

\* cited by examiner

Primary Examiner—Gary L. Kunz
Assistant Examiner—Robert S. Landsman
(74) Attorney, Agent, or Firm—McDonnell Boehnen Hulbert & Berghoff

(57) ABSTRACT

The present invention relates to a novel-mammalian methadone-specific opioid receptor protein and genes that encode such a protein. The invention is directed toward the isolation, characterization and pharmacological use of mammalian methadone-specific opioid receptor proteins. The invention specifically provides isolated complementary DNA copies of mRNA corresponding to the rat homologue of the mammalian methadone-specific opioid receptor gene. Also provided are recombinant expression constructs capable of expressing the mammalian methadone-specific opioid receptor genes of the invention in cultures of transformed prokaryotic and eukaryotic cells, as well as such cultures of transformed cells that synthesize the mammalian methadone-specific opioid receptor proteins encoded therein. The invention also provides methods for screening compounds in vitro that are capable of binding to the mammalian methadone-specific opioid receptor proteins of the invention, and further characterizing the binding properties of such compounds in comparison with known opioid receptor agonists and antagonists.

2 Claims, 10 Drawing Sheets

FIG. 1A

```
CCGAGGAGCCATTCCCAGCCGCAGCAGACCCCAATCTAGAGTGAGAGTCATTGCTCAGTCCACTGTGCTCC        71
TGCCTGCCCGCCTTTCTGCTAAGCATTGGGGTCTATTTGCGCCCAGCTTCTGAAGAGGCTGTGTGCCG          142

TTGGAGAACTGTACTGAGTGGCTTTGCAGGGTGACAGACATGGAGTCCCTGTTCCCTGCTCCATACTGGGAG       214
                    M  E  S  L  F  P  A  P  Y  W  E

GTCTTGCATGGCAGCCACTTTCAAGGGAACCTGTCCCTCCTAAATGAGACCGTACCCCACCACTGCTCCTC        286
 V  L  H  G  S  H  F  Q  G  N  L  S  L  L  N  E  T  V  P  H  H  L  L  L
                          A                       A

AATGCTAGTCACAGCGCCTTCCTGCCCCTTGGACTCAAGGTCACCATCGTGGGGCTCATCTTGGCTGTGTGC       358
 N  A  S  H  S  A  F  L  P  L  G  L  K  V  T  I  V  G  L  I  L  A  V  C
 A                             I

ATCGGGGGCCTCCTGGGGAACTGCCTCGTGATGTATGTCATCCTCAGGACACACCCCAAGATGAAGACAGCTACC    430
 I  G  G  L  L  G  N  C  L  V  M  Y  V  I  L  R  T  P  K  M  K  T  A  T
                 I                                                   II

AACATTTACATATTTAATCTGGCACTGGCTGATACCCTGGTCTTGCTAACACTGCCCTTCCAGGGCACAGAC       502
 N  I  Y  I  F  N  L  A  L  A  D  T  L  V  L  L  T  L  P  F  Q  G  T  D
 N                                   II

ATCCTACTGGGCTTCTGGCCATTTGGGAAAGCACTCTGCAAGACTGTCATTGCTATCGACTACTACAACATG       574
 I  L  L  G  F  W  P  F  G  K  A  L  C  K  T  V  I  A  I  D  Y  Y  N  M
                                                      III

TTTACCAGCACTTTTACTCTGACCGCCATGAGCGTAGACCGCTATGTGGCTATCTGCCACCCTATCCGTGCC      646
 F  T  S  T  F  T  L  T  A  M  S  V  D  R  Y  V  A  I  C  H  P  I  R  A
 III
```

FIG. 1B

```
CTTGATGTTCGGACATCCAGCAAAGCCCAGGCTGTGTTAATGTGGCCCATATGGGCCCTGGCTTCAGTGGTTGGT   718
 L  D  V  R  T  S  S  K  A  Q  A  V  N  V  A  I  W  A  L  A  S  V  V  G
                                                                    IV

GTTCCTGTTGCCATCATGGGTTCAGCACAAGTGGAAGATGAAGAGATCGAGTGCCTGGTGGAGATCCCTGCC      790
 V  P  V  A  I  M  G  S  A  Q  V  E  D  E  E  I  E  C  L  V  E  I  P  A
           IV

CCTCAGGACTATTGGGGCCCTGTATTCGCCATCTGCATCTTCCTTTTTCCTTCATCATCCCTGTGCTGATC       862
 P  Q  D  Y  W  G  P  V  F  A  I  C  I  F  L  F  S  F  I  I  P  V  L  I
                                    V

ATCTCTGTGTGCTACAGCCTCTACATGATTCGACGACTTCGTGGTGTCCGTCTGCTTCAGGCTCCCGGAGAAG    934
 I  S  V  C  Y  S  L  M  I  R  R  L  R  G  V  R  L  L  S  G  S  R  E  K
          V

GACCGAAACCTGCGGCGTATCACTCGACTGGTGCTGGTAGTGGTGGCTGTGTTTGTGGGCTGCTGGACGCCT     1006
 D  R  N  L  R  R  I  T  R  L  V  L  V  V  V  A  V  F  V  G  C  W  T  P
                                                      VI

GTGCAGGTGTTTGTCCTGGTTCAAGGACTGGGTGTTCAGCCAGGTTCAGAGACTGCAGTTGCCATCCTGCGC     1078
 V  Q  V  F  V  L  V  Q  G  L  G  V  Q  P  G  S  E  T  A  V  A  I  L  R
    VI

TTCTGCACAGCCCTGGGCTACGTGCAACAGTTGTCTAATCCCATTCTCTATGCTTTCCTGGATGAGAACTTC    1150
 F  C  T  A  L  G  Y  V  H  S  C  L  N  P  I  L  Y  A  F  L  D  E  N  F
                  VII
```

FIG. 1C

```
AAGGCCTGCTTTAGAAAGTTCTGCTGTGCTTCATCCCTGCACCGGGAGAGATGCAGGTTTCTGATCGTGTGCGG    1222
 K  A  C  F  R  K  F  C  C  A  S  S  L  H  R  E  M  Q  V  S  D  R  V  R
                                                          *
ACGATTGCCAAGGATGTTGGCCTTGGTTGCAAGACTTCTGAGACAGTACCACGGCCAGCATGACTAGGCGTG      1294
 T  I  A  K  D  V  G  L  G  C  K  T  S  E  T  V  P  R  P  A

GACCTGCCCATGGTGCCTGTCAGCCCACAGAGACCCATCCTACACCCAACACGGAGCTCACACAGGTCACTGC    1366
TCTCTAGGTTGACCCTGAACCTTGAGCATCTGGAGCCCTTGAATGGCTTTTCTTTTGGATCAGGATGCTCAGT    1438
CCTAGAGGAAGACC
```

FIG. 2A

```
LC132                        MESLFPAPYWEVL
Rat μ-Opioid Receptor        MDSSTGPGNTSDCSDPLAQASCSPAPGSWLNLS
Mouse δ-Opioid Receptor                              MELVPSARAELQSS
Mouse κ-Opioid Receptor              MESPIQIFRGDPGPTCSPSACLLP I
LC132      HGSHFQGNLSLLNETVPHHLLLNASHSAFLPLGLKVTIVGLILAVCIGLLGNCL
(μ-OR)     HVDGNQSDPCGLNRTGLGGNDSLCPQTGSPSMVTAITIMALYSIVCVVGLFGNFL
(δ-OR)     PLVNLSDAFPSAFPSAGANASGSPGARSASSLALAIAITALYSAVCAVGLLGNVL
(κ-OR)     NSSSWFPNWAESDSNGSVGSEDQQLESAHISPAIPVIITAVYSVVFVVGLVGNSL II
LC132      VMYVILRTPKMKTATNIYIFNLALADTLVLLTLPFQGTDILLGFWPFGKALCKTV
(μ-OR)     VMYVIVRYTKMKTATNIYIFNLALADALATSTLPFQSVNYLMGTWPFGTILCKIV
(δ-OR)     VMFGIVRYTKLKTATNIYIFNLALADALATSTLPFQSAKYLMETWPFGELLCKAV
(κ-OR)     VMFVIIRYTKMKTATNIYIFNLALADALVTTTMPFQSAVYLMNSWPFGDVLCKIV III                                          IV
LC132      IAIDYYNMFTSTFTLTAMSVDRYVAICHPIRALDVRTSSKAQAVNVAIWALASVV
(μ-OR)     ISIDYYNMFTSIFTLCTMSVDRYIAVCHPVKALDFRTPRNAKIVMVCNWILSSAI
(δ-OR)     LSIDYYNMFTSIFTLTMMSVDRYIAVCHPVKALDFRTPAKAKLIMICIWVLASGV
(κ-OR)     ISIDYYNMMFTSIFTLTMMSVDRYIAVCHPVKALDFRTPLKAKIIMICIWLLASSV
```

FIG. 2B

```
                                                                        V
LC132    GVPVAIMGSAQ  VEDEEIECLVEIPAP QDYWGPVEAICIFLFSFIIPVLIISV
(μ-OR)   GLPVMFMATTK  YRQGSIDCTLTFSHP TWYWENLLKICVFIFAFIMPILIITV
(δ-OR)   GVPIMVMAVTQ  PRDEAVVCMLQFPSP SWYWDTVTKICVFLEAFVVPILIITV
(κ-OR)   GISAIVLGGTKVREDVDVIECSLQFPDDEYSWWDLFMKICVFVFAFVIPVLIIIV

VI
LC132    CYSLMIRRLRGVRLLSGSREKDRNLRRITRLVLVVVAVFVGCWTPVQVFVLVQGL
(μ-OR)   CYGLMILRLKSVRMLSGSKKKDRNLRRITRMVLVVVAVFIVCWTPIHIYVIIKAL
(δ-OR)   CYGLMLLRLRSVRLLSGSKKKDRSLRRITRMVLVVVGAFVVCWAPIHIFVIVWTL
(κ-OR)   CYTLMILRLKSVRLLSGSRKKDRNLRRITKLVLVLVVVAVFIICWTPIHIFILVEAL

VII
LC132    GVQPGSETAVAIL RFCTALGYVHSCLNPILYAFLDENFKACFRKFCCASSLHRE
(μ-OR)   ITIPETTFQTVSW HFCIALGYTMSCLMPVLYAFLDEMFKRCFREFCIPTSSTIE
(δ-OR)   VDINRRDPLVVAALHLCIALGYAMSSLMPVLYAFLDEMFKRCFRQLCRTPCGRQE
(κ-OR)   GSTSHSTAALSSY YFCIALGYTMSSLMPVLYAFLDEMFKRCFRDFCFPIKMRME

LC132    MQVSDRVRTIAKDVGLGCKTSETVPRPA      367
(μ-OR)   QQNSTRVRQNTREHPSTANTVDRTNHQLENLEAETAPLP  398
(δ-OR)   PGSLRRPRQATTRERVTACTPSDGPGGGAAA   372
(κ-OR)   RQSTNRVRNTVQDPASMRDVGGMNKPV       380
```

MAMMALIAN METHADONE-SPECIFIC OPIOID RECEPTOR GENE AND USES

This application is a divisional of U.S. Ser. No. 09/170,331, filed Oct. 13, 1998, now U.S. Pat. No. 6,028,175, which is a divisional of U.S. Ser. No. 09/911,245, filed Aug. 15, 1997, now U.S. Pat. No. 5,821,067, issued Oct. 13, 1998, which is a divisional of U.S. Ser. No. 08/149,093, filed Nov. 8, 1993, now U.S. Pat. No. 5,658,783, issued Aug. 15, 1997.

This invention was made with government support under National Institute of Health grants R01 MH48991. The government has certain rights to this invention.

BACKGROUND OF THE INVENTION

1. Field of the Invention

This invention relates to opioid receptors from mammalian species and the genes corresponding to such receptors. Specifically, the invention relates to the isolation, cloning and sequencing of complementary DNA (cDNA) copies of messenger RNA (mRNA) encoding a novel mammalian opioid receptor gene. The invention also relates to the construction of recombinant expression constructs comprising cDNA of this novel opioid receptor gene, said recombinant expression constructs being capable of expressing opioid receptor protein in cultures of transformed prokaryotic and eukaryotic cells. Production of the receptor protein in such cultures is also provided. The invention relates to the use of such cultures of such transformed cells to produce homogeneous compositions of the novel opioid receptor protein. The invention also provides cultures of such cells producing this opioid receptor protein for the characterization of novel and useful drugs. Antibodies against and epitopes of this novel opioid receptor protein are also provided by the invention.

2. Background of the Invention

The use (and abuse) of opiates, archetypally opium and morphine, have been known since antiquity (reviewed in Brownstein, 1993, Proc. Natl. Acad. Sci. USA 90: 5391–5393). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (see DiChara & North, 1992, Trends in Phamacol. Sci. 13: 185–193 for review). Accompanying this finding of an endogenous opiate was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution; these comprise the $\mu$, $\delta$, $\kappa$ and $\sigma$ receptors (the $\sigma$ receptor has been determined to be a non-opioid receptor with cross-reactivity to some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. USA 89: 12048–12052 disclosed the isolation of a cDNA copy of the mouse $\delta$-opioid receptor by expression cloning.

Evans et al., 1992, Science 258: 1952–1955 disclose the isolation of a cDNA copy of the mouse $\delta$-opioid receptor by expression cloning.

Chen et al., 1993, Molec. Pharmacol. 44: 8–12 disclose the isolation of a cDNA copy of the rat $\mu$-opioid receptor.

Yasuda et al., 1993, Proc. Natl. Acad. Sci. USA 90: 6736–6740 disclose the isolation of a cDNA copy of each of the mouse $\kappa$- and $\delta$-opioid receptor.

Bzdega et al., 1993, Proc. Natl. Acad. Sci. USA 90: 9305–9309 disclose the isolation and chromosomal location of the $\delta$-opioid receptor in the mouse.

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that hundreds, if not thousands, of chemical compounds must be tested in order to identify a single effective therapeutic agent that does not engender unacceptable levels of undesirable or deleterious side effects. There is an increasing need for economical methods of testing large number of chemical compounds to quickly identify those compounds that are likely to be effective in treating disease.

This is of particular importance for psychoactive and psychotropic drugs, due to their pharmacological importance and their potential to greatly benefit or greatly harm human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human opioid receptor molecules in vitro would provide an efficient and economical means for rational drug design and rapid screening of potentially useful compounds. For these and other reasons, development in vitro screening methods for psychotropic drugs has numerous advantages and is a major research goal in the pharmaceutical industry.

SUMMARY OF THE INVENTION

The present invention relates to the cloning, expression and functional characterization of a mammalian methadone-specific opioid receptor (MSOR) gene. The invention comprises nucleic acids having a nucleotide sequence of a novel mammalian MSOR gene. The nucleic acids provided by the invention comprise a complementary DNA (cDNA) copy of the corresponding mRNA transcribed in vitro from the MSOR genes of the invention. Also provided are the deduced amino acid sequence of the cognate protein of the cDNA provided by the invention.

This invention provides nucleic acids, nucleic acid hybridization probes, recombinant eukaryotic expression constructs capable of expressing the MSOR receptors of the invention in cultures of transformed cells, such cultures of transformed eukaryotic cells that synthesize the MSOR receptors of the invention, homogeneous compositions of the MSOR receptor protein, and antibodies against and epitopes of the MSOR receptor protein of the invention. Methods for characterizing these receptor proteins and methods for using these proteins in the development of agents having pharmacological uses related to these receptors are also provided by the invention.

In a first aspect, the invention provides a nucleic acid having a nucleotide sequence encoding a mammalian methadone-specific opioid receptor. In a preferred embodiment, the nucleic acid encodes the rat MSOR receptor. In this embodiment of the invention, the nucleotide sequence includes 1452 nucleotides of the rat MSOR cDNA comprising 1101 nucleotides of coding sequence, 181 nucleotides of 5' untranslated sequence and 170 nucleotides of 3' untranslated sequence. In this embodiment of the invention, the nucleotide sequence of the MSOR receptor consists essentially of the nucleotide sequence depicted in FIGS. 1A through 1C (SEQ ID No:3). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding MSOR disclosed herein.

The corresponding MSOR protein molecule, having the deduced amino acid sequence consisting essentially of the sequence shown in FIGS. 1A through 1C (SEQ ID No.:4), is also claimed as an aspect of the invention. The use of the term "consisting essentially of" herein is as described above. Similarly, the MSOR protein molecule, having the deduced amino acid sequence consisting essentially of the sequence shown in FIGS. 1A through 1C (SEQ ID No.:4), is also claimed as an aspect of the invention. MSOR protein molecules provided by the invention are understood to have substantially the same biological properties as the MSOR protein molecule encoded by the nucleotide sequence described herein.

In another aspect, the invention comprises a homogeneous composition of the 47 kD mammalian MSOR transporter or derivative thereof, said size being understood to be the size of the protein before any post-translational modifications thereof. The amino acid sequence of the MSOR transporter or derivative thereof preferably consists essentially of the amino acid sequence of the MSOR transporter protein shown in FIGS. 1A through 1C (SEQ ID No:4).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the MSOR receptor gene in various tissues of mammals, including humans. It is also an object of the present invention to provide nucleic acid hybridization probes derived from the sequences of mammalian MSOR receptor genes of the invention to be used for the detection and diagnosis of genetic diseases. It is an object of this invention to provide nucleic acid hybridization probes derived from the DNA sequences of the mammalian MSOR receptor genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of MSOR receptor-specific antibodies, or useful as competitors of MSOR receptor molecules for agonist, antagonist or drug binding, or to be used for the production of inhibitors of the binding of agonists or antagonists or analogues thereof to such MSOR receptor molecules.

The present invention also provides antibodies against and epitopes of the mammalian MSOR receptor molecules of the invention. It is an object of the present invention to provide antibodies that are immunologically reactive to the MSOR receptors of the invention. It is a particular object to provide monoclonal antibodies against these MSOR receptors. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of a mammalian MSOR receptor of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the mammalian MSOR receptor proteins of the invention. Chimeric antibodies immunologically reactive against the MSOR receptor proteins of the invention are also within the scope of this invention.

The present invention provides recombinant expression constructs comprising a nucleic acid encoding a mammalian MSOR receptor of the invention wherein the construct is capable of expressing the encoded MSOR receptor in cultures of cells transformed with the construct. Preferred embodiments of such constructs comprise the MSOR receptor cDNA depicted in FIGS. 1A through 1C (SEQ ID NO.:3), such constructs being capable of expressing the MSOR receptor encoded therein in cells transformed with the construct.

The invention also provides cultures cells transformed with the recombinant expression constructs of the invention, each such culture being capable of and in fact expressing the mammalian MSOR receptor encoded in the transforming construct.

The present invention also includes within its scope protein preparations of prokaryotic and eukaryotic cell membranes containing the MSOR receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian MSOR receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects.

The present invention is also useful for the detection of analogues, agonists or antagonists, known or unknown, of the mammalian MSOR receptors of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A through 1C illustrates the nucleotide (SEQ ID No.:3) and amino acid (SEQ ID No.:4) sequences of the rat methadone-specific opioid receptor.

FIGS. 2A and 2B presents an amino acid sequence comparison between the rat methadone-specific opioid receptor protein (LC132) and the rat μ-opioid receptor, and the mouse δ- and κ-opioid receptor proteins.

FIGS. 4A through 4C illustrates in situ hybridization of rat brain sections with a nucleic acid hybridization probe specific for the methadone-specific mammalian opioid receptor of the invention.

DETAILED DESCRIPTION OF THE PREFERRED EMBODIMENTS

Figure 3A:
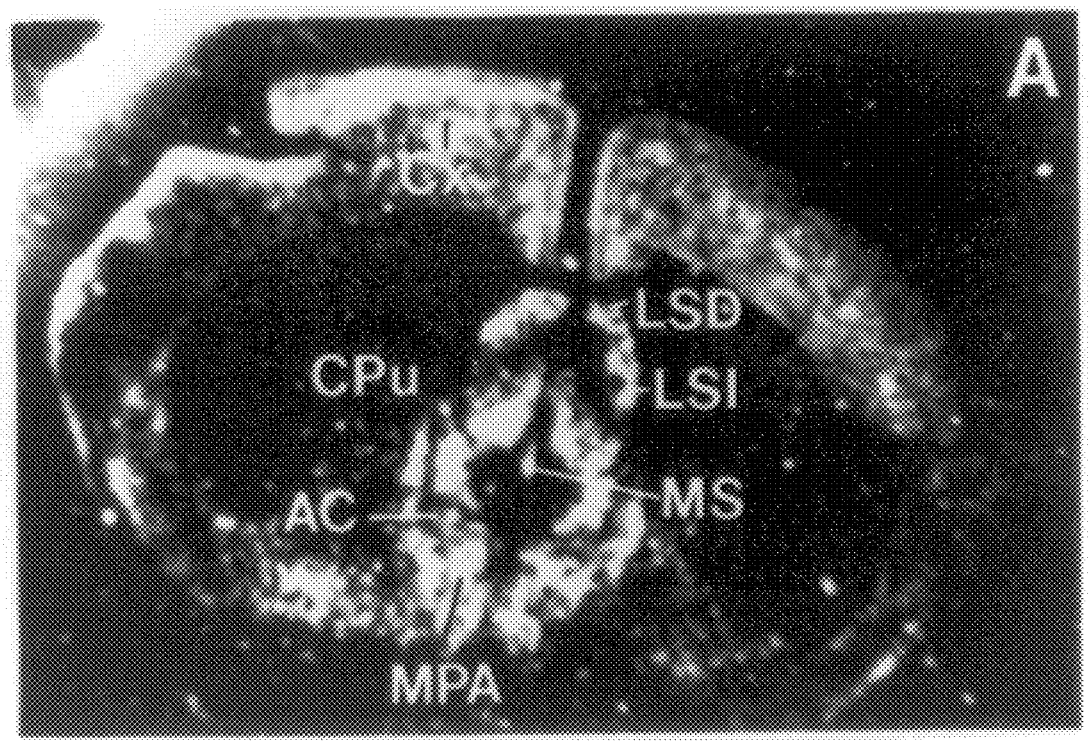
FIGS. 3A and 3B presents affinity binding experiment results of $^3$H-methadone binding to COS-7 cells (Panel A) and to COS-7 cells expressing the mammalian methadone-specific opioid receptor of the invention.

The term "mammalian methadone-specific opioid receptor (MSOR)" as used herein refers to proteins consisting essentially of, and having substantially the same biological activity as, the protein encoded by the nucleic aid depicted in FIGS. 1A through 1C (SEQ ID No.:3). This definition is intended to encompass natural allelic variations in the disclosed MSOR sequence. Cloned nucleic acid provided by the present invention may encode MSOR protein of any species of origin, including, for example, mouse, rat, rabbit, cat, and human, but preferably the nucleic acid provided by the invention encodes MSOR receptors of mammalian, most preferably rat and human, origin.

The nucleic acid hybridization probes provided by the invention comprise DNA or RNA consisting essentially of the nucleotide sequence of the MSOR receptor, depicted in FIGS. 1A through 1C (SEQ ID No.:3), or any portion thereof effective in nucleic acid hybridization. Mixtures of such nucleic acid hybridization probes are also within the scope of this embodiment of the invention. Nucleic acid probes as provided herein are useful for detecting MSOR receptor gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are also useful for Southern hybridization of mammalian, preferably human, genomic DNA for screening for restriction fragment length polymorphism (RFLP) associated with certain genetic disorders.

The production of proteins such as the MSOR receptor molecule from clones genes by genetic engineering means is well known in this art. The discussion which follows is accordingly intended as an overview of this field, and is not intended to reflect the full state of the art.

DNA encoding an MSOR receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the MSOR receptor disclosed herein. Probes may be labeled with a detectable group such as a fluorescent group, a radioactive atom or a chemiluminescent group in accordance with known procedures and used in conventional hybridization assays, as described in greater detail in the Examples below. In the alternative, MSOR derived nucleic acid sequences may be obtained by use of the polymerase chain reaction (PCR) procedure, using PCR oligonucleotide primers corresponding to nucleic acid sequence information derived from an MSOR receptor as provided herein. See U.S. Pat. Nos. 4,683,195 to Mullis et al. and 4,683,202 to Mullis.

The MSOR receptor protein may be synthesized in host cells transformed with a recombinant expression construct comprising a nucleic acid encoding the MSOR receptor cDNA. Such recombinant expression constructs can also be comprised of a vector that is a replicable DNA construct. Vectors are used herein either to amplify DNA encoding an MSOR receptor and/or to express DNA encoding an MSOR receptor gene. For the purposes of this invention, a recombinant expression construct is a replicable DNA construct in which a nucleic acid encoding an MSOR receptor is operably linked to suitable control sequences capable of effecting the expression of the MSOR receptor in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is RcRVS (Invitrogen, San Diego, Calif.). Transformed host cells are cells which have been transformed or transfected with recombinant expression constructs made using recombinant DNA techniques and comprising nucleic acid encoding an MSOR protein. Preferred host cells are COS-7 cells (Gluzman, 1981, Cell 23: 175–182) and Ltk⁻ cells. Transformed host cells may express the MSOR receptor protein, but host cells transformed for purposes of cloning or amplifying nucleic acid hybridization probe DNA need not express the receptor. When expressed, the MSOR receptor of the invention will typically be located in the host cell membrane. See, Sambrook et al., ibid.

Cultures of cells derived from multicellular organisms are a desirable host for recombinant MSOR receptor protein synthesis. In principal, any hither eukaryotic cell culture is useful, whether from vertebrate or invertebrate culture. However, mammalian cells are preferred, as illustrated in the Examples. Propagation of such cells in cell culture has become a routine procedure. See *Tissue Culture,* Academic Press, Kruse & Patterson, editors (1973). Examples of useful host cell lines are human 293 cells, VERO and HeLa cells, Chinese hamster ovary (CHO) cell lines, mouse Ltk⁻ cell lines and WI138, BHK, COS-7, CV, and MDCK cell lines. COS-7 cells and Ltk⁻ cells are preferred.

The invention provides homogeneous compositions of mammalian methadone-specific opioid receptor protein produced by transformed eukaryotic cells as provided herein. Each such homogeneous composition is intended to be comprised of the MSOR receptor protein that comprises at least 90% of the protein in such a homogenous composition. The invention also provides membrane preparations from cells expressing the MSOR receptor protein as the result of transformation with a recombinant expression construct, as described herein.

Mammalian methadone-specific opioid receptor proteins made from cloned genes in accordance with the present invention may be used for screening opioid analogues, or agonists or antagonists of opioid binding, or for determining the amount of such agonists or antagonists present in a solution of interest (e.g., blood plasma, cerebrospinal fluid or serum). For example, host cells may be transformed with a recombinant expression construct of the present invention, a mammalian MSOR receptor expressed in those host cells, and the cells or membranes thereof used to screen compounds for their effect on opioid agonist binding activity. By selection of host cells that do not ordinarily express a MSOR receptor, pure preparations of membranes containing the transporter can be obtained.

The recombinant expression constructs of the present invention are useful in molecular biology to transform cells which do not ordinarily express an MSOR receptor to thereafter express this receptor. Such cells are useful as intermediates for making cell membrane preparations useful for receptor binding activity assays, which are in turn useful for drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful in molecular biology to detect, isolate, characterize and identify novel endogenous opioid receptor agonists and antagonists found in plasma, serum, lymph, cerebrospinal fluid, seminal fluid, or other potential sources of such compounds. This utility thereby enables rational drug design of novel therapeutically-active drugs using currently-available techniques (see Walters, "Computer-Assisted Modeling of Drugs", in Klegerman & Groves, eds., 1993, *Pharmaceutical Biotechnology,* Interpharm Press: Buffalo Grove, Ill., pp. 165–174).

The recombinant expression constructs of the present invention may also be useful in gene therapy. Cloned genes of the present invention, or fragments thereof, may also be used in gene therapy carried out using homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing MSOR receptor gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding MSOR receptor gene, and potential pathological conditions related thereto.

The invention also provides antibodies that are immunologically reactive to the MSOR receptor protein or epitopes thereof provided by the invention. The antibodies provided by the invention may be raised, using methods well known in the art, in animals by inoculation with cells that express an MSOR receptor or epitopes thereof, cell membranes from such cells, whether crude membrane preparations or membranes purified using methods well known in the art, or purified preparations of proteins, including fusion proteins, particularly fusion proteins comprising epitopes of the MSOR receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the MSOR receptor provided by the invention, or any cell or cell line that expresses the MSOR receptor of the invention, or any epitope thereof, as a result of molecular or genetic engineering, or that has been treated to increase the expression of an endogenous or heterologous MSOR receptor protein by physical, biochemical or genetic means. Preferred cells are *E. coli* and insect SF9 cells, most preferably *E. coli* cells, that have been transformed with a recombinant expression construct of the invention encoding an MSOR receptor protein, and that express the receptor therefrom.

The present invention also provides monoclonal antibodies that are immunologically reactive with an epitope derived from an MSOR receptor of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an MSOR receptor of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$'_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an MSOR receptor, made by methods known to those of skill in the art.

The present invention also encompasses an epitope of an MSOR receptor of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an MSOR receptor-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Mammalian Opioid Receptor Probe by Random PCR Amplification of Rat Brain-derived cDNA Using Degenerate Oligonucleotide Primers In order to clone novel mammalian G-protein coupled receptors, cDNA prepared from RNA from different regions of rat brain was used as template for a polymerase chain reaction (PCR)-based random cloning experiment. PCR was performed using a pair of degenerate oligonucleotide primers corresponding to the putative third and seventh transmembrane regions of a mouse δ-opioid receptor (Kieffer et al., 1992, Proc. Natl. Acad. Sci. USA 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as follows. Total RNA was isolated from various rat brain regions by the guanidinium thiocyanate method (Chirgwin et al., 1979, Biochemistry 18: 5294–5299). First-strand cDNA was prepared from rat brain RNA using standard techniques (see Sambrook et al., 1990, *Molecular Cloning: A Laboratory Manual*, Cold Spring Harbor Press, Cold Spring Harbor Laboratory, N.Y.) using murine reverse transcriptase (BRL, Gaithersburg, Md.) and oligo-dT priming (Sambrook et al., ibid.). The rat brain cDNA preparation was then subjected to 35 cycles of PCR amplification using 500 picomoles of degenerate oligonucleotide primers having the following sequence:

Primer III (sense):
ATGAATTCAC(G/A/C/T)(A/G)T(G/C)ATGAG(C/T)
GT(G/C)GAC(C/A)G(C/A)TA (SEQ ID NO:1)
and Primer VII (antisense):
TTGTCGAC(G/A)TA(G/A)AG(A/G)A(T/C)(G/A/C/T)GG(G/A)TT (SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). Each PCR amplification cycle consisted of incubations at 94° C. for 1 min (denaturation), 50° C. for 1.5 min (annealing), and 72° C. for 1.5 min (extension).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a ($^{32}$P)-dCTP-labeled radioactive nucleic acid probe comprising a full-length mouse δ-opioid receptor cDNA at a concentration of 1×10$^4$ cpm/mL under low stringency hybridization conditions (35% formamide, 5×standard citrate saline (SSC; wherein 1×SSC is 0.15M NaCl/0.015M sodium citrate, pH 7.0), 5×Denhardt's solution (wherein 1×Denhardt's solution is 0.02 g/mL each of bovine serum albumin, Ficoll and polyvinylpyrrolidone)) at 37° C. overnight. After hybridization, the filters were washed in a solution of 2×SSC/0.1% sodium dodecyl sulfate (SDS) at 55° C. and then exposed to X-ray film (XAR-5, Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. USA 74: 5463–5467) using Sequenase® (U.S. Biochemical Corp., Cleveland, Ohio).

EXAMPLE 2

Isolation of a Novel Mammalian Opioid Receptor cDNA

One of the PCR products (termed LC132) was isolated and sequenced in this way and was found to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)-primed rat brain cDNA. Plaque-containing nitrocellulose filters were hybridized with a ($^{32}$P)-dCTP-labeled, randomly-primed hybridization probe consisting of a fragment of the LC132 PCR product under high stringency conditions (which were identical to the low stringency conditions described above except that the hybridization solution was 50% formamide and hybridized filters were washed at 0.5×SSC/0.1% SDS). Positively-hybridizing λgt11 clones were plaque purified (i.e., grown, replated and re-infected in bacteria until all phage plaques hybridized to the probe, indicating that all plaques arose from phage containing the same insert; see Sambrook et al., ibid.) and analyzed by restriction enzyme digestion. An open reading frame was found on a 3.1 kilobase (kb) EcoRI-digested DNA fragment and was analyzed as follows.

Nucleotide sequence analysis performed essentially as described in Example 1 revealed the sequence shown in FIGS. 1A through C (SEQ ID No.: 3). The putative protein product of the gene is also shown in FIGS. 1A through C (SEQ ID No:4). The sequence was found to have an open reading frame comprising 1101 nucleotides encoding a protein 367 amino acids in length, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains (using the algorithm of Eisenberg et al. (1984, J. Molec. Biol. 179: 125–142)) are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic aid was determined to be a novel mammalian opioid receptor. Comparison of the amino acid sequence of the novel receptor with the amino acid sequences of other known mammalian opioid receptors supported this conclusion.

The predicted amino aid sequences of this novel opioid receptor, the rat μ-opioid receptor (Chen et al., ibid.), the mouse δ-opioid receptor (Evans et al., ibid. and Kieffer et al., ibid.) and the mouse κ-opioid receptor (Yasuda et al., ibid.) are aligned in FIGS. 2A and 2B. Overbars indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. A more detailed comparison of these amino acid sequences are quantified in Table I, showing the percentage extent of homology in pairwise fashion between the different opioid receptors. Comparisons are made individually at each transmembrane domain (TMI–TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is an opioid receptor.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk$^-$ cells (for stable expression assays), and cell membranes (COS-7) or cell lines (Ltk$^-$) were generated that expressed the receptor protein in cellular membranes at the cell surface. Such cells and membranes isolated from such cells were used for biochemical characterization experiments described below.

The entire coding region of the receptor cDNA insert was amplified using PCR as described above with primers specific for sequences in the 5' and 3' untranslated sequences; such PCR primers advantageously contained restriction enzyme digestion recognition sites at the 5' termini such that digestion with said restriction enzymes allowed facile cloning of the receptor cDNA into the mammalian expression construct RcRSV (Invitrogen, San Diego, Calif.). PCR products generated in this way were subcloned into the RcRSV vector using conventional techniques (see Sambrook et al., ibid.) and the orientation of the inserted cDNA confirmed by restriction enzyme digestion analysis of insert-containing subclones. Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. Such membranes were harvested from cells grown on 15 cm plates by pelleting the cells at 20,000 rpm in a solution of 50 mM Tris-HCl (pH 7.4). The protein concentration was adjusted to 15–80 μg/sample for each of the binding studies described below.

These recombinant expression constructs were also introduced into Ltk$^-$ cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. (1988, Nature 336: 783–787). In binding experiments, increasing amounts of membrane protein (from 15–80 μg) were incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): ($^3$H)-Tyr-DAla-Gly-Met-Phe-Gly-ol (DAMGO; μ-opioid receptor agonist), ($^3$H)-c[D-penicillamine$^2$, D-penicillamine$^5$]enkephalin (DPDPE; δ agonist), ($^3$H)-U-69,593 (κ agonist), ($^3$H)-diprenorphine (μ agonist), ($^3$H)-bremacozine (κ agonist), ($^3$H)-dihydromorphine (μ agonist), ($^3$H)-ethylketocyclazocine (κ agonist) or ($^{125}$I)-β-endorphin. Although low levels of specific binding were seen using ($^3$H)-naloxone (μ antagonist), the significance of these results was compromised by the fact that untransfected COS-7 and Ltk$^-$ cells also shown endogenous low levels of specific ($^3$H)-naloxone binding.

Surprisingly, however, specific binding was found using ($^3$H)-methadone. The results of Scatchard analysis of the methadone binding data are shown in FIGS. 4A and 4B. For Scatchard analysis experiments, 0.25 ml aliquots of crude plasma membrane homogenate from transfected cell cultures was incubated in duplicate with increasing concentrations of ($^3$H)methadone (70.3 Ci/mmol; 10–3000 pM final concentration) under conditions described above. The estimated value for $B_{max}$ was derived from these data were obtained using the LIGAND computer program. FIG. 4A of FIG. 3 shows the results of radiolabeled methadone binding with untransfected COS-7 cells; similar results were found with Ltk$^-$ cell membranes. These results demonstrate no or negligible amounts of endogenous methadone binding by these cell membranes. FIG. 4B shows the results using COS-7 cells transfected with the RcRSV-LC132 expression construct. The levels of specific binding shown in this graph correspond to a dissociation constant ($K_D$) of about $10^{-10}$M for methadone and a $B_{max}$ of about 400–450 femtomoles/μg protein for the novel mammalian opioid receptor expressed by these cells.

Thus, the novel mammalian opioid receptor disclosed herein has the heretofore unknown property of exhibiting specific binding to the opiate analog, methadone, while showing no specific binding to a variety of other known opioid receptor agonists and antagonists. These results support the conclusion that the receptor disclosed herein is a completely novel and heretofore unsuspected member of the opioid receptor family, termed herein therefore MSOR.

EXAMPLE 4

Brain Tissue Distribution of Methadone-Specific Opioid Receptor Expression

The distribution of mRNA corresponding to expression of the MSOR receptor gene in various regions of the rat brain was determined by in situ hybridization of rat brain slices. Rat brain sections were made and were hybridized with an ($^{35}$S)-CTP-labeled synthetic RNA (termed a riboprobe; see Promega Biotech Riboprobe System, Madison, Wis.) using conventional techniques.

In situ hybridization of rat brain section was performed as follows. Male Sprague-Dawley rats (200 g) were anesthetized and perfused at 40° C. with 1 L of 4% paraformaldehyde in borate buffer, pH 9.5 (fixation buffer). Brains were dissected and incubated in fixation buffer for 8 h, then further incubated overnight in fixation buffer containing 10% sucrose. Brains were then sectioned serially into series of 15 μm slices with a sliding microtome. Sections were prepared and hybridized as described in Arriza et al., 1988, Neuron 1: 887–900. A 600 bp fragment of the MSOR cDNA was subcloned into a pBKS vector (Stratagene) and used to synthesize a ($^{35}$S)-CTP radiolabeled antisense cRNA probe (see Sambrook et al., ibid.) Sections were hybridized at 65° C. for 24 h with $^{35}$S-labeled probe (~1×10$^7$ cpm/ml) in 65% formamide, 0.26M NaCl, 1.3×Denhardt's solution, 13 mM Tris (pH 8.0), 1.3 mM EDTA and 13% dextran sulfate. Slides were washed in 4×SSC (0.6M NaCl, 0.06M Na citrate), digested with RNase (20 pg/ml) for 30 min at 37° C., and then rinsed to a final stringency of 0.1×SSC at 65° C. for 30 min. Sections were dehydrated, dipped in NTB-2 emulsion, and developed after 21 days.

Figure 3B:
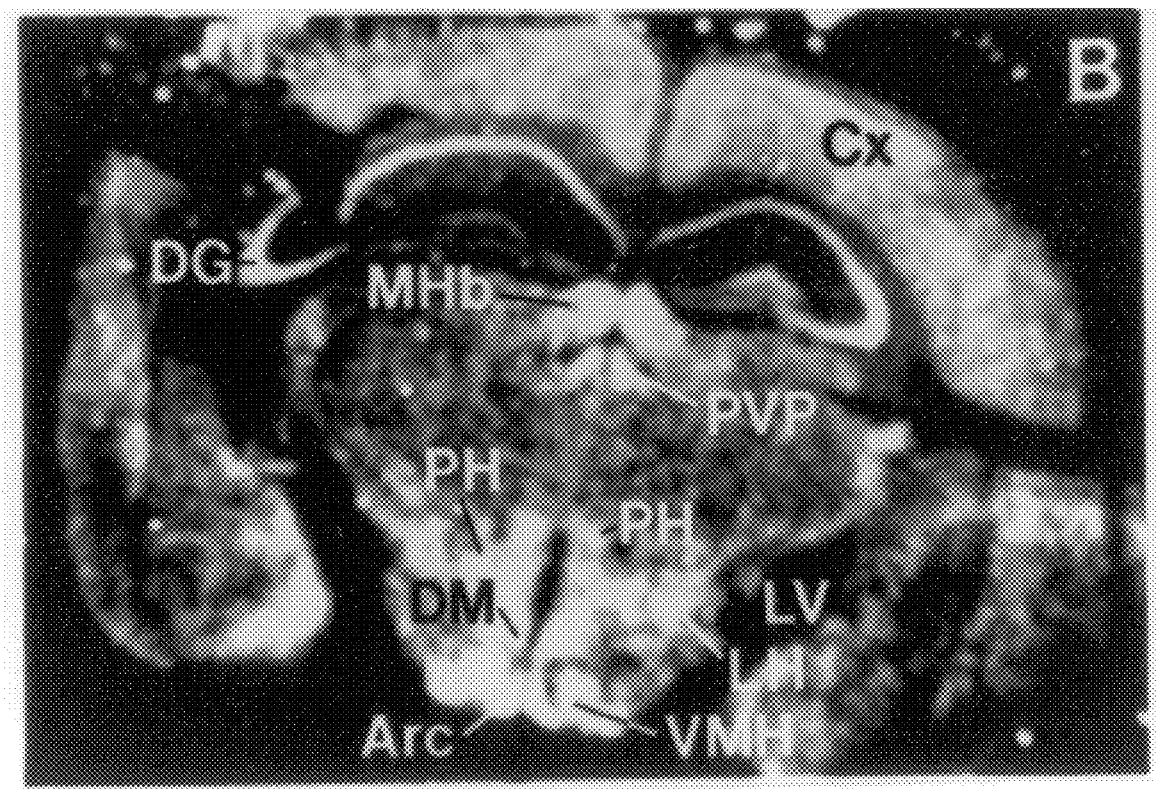
Figure 3C:
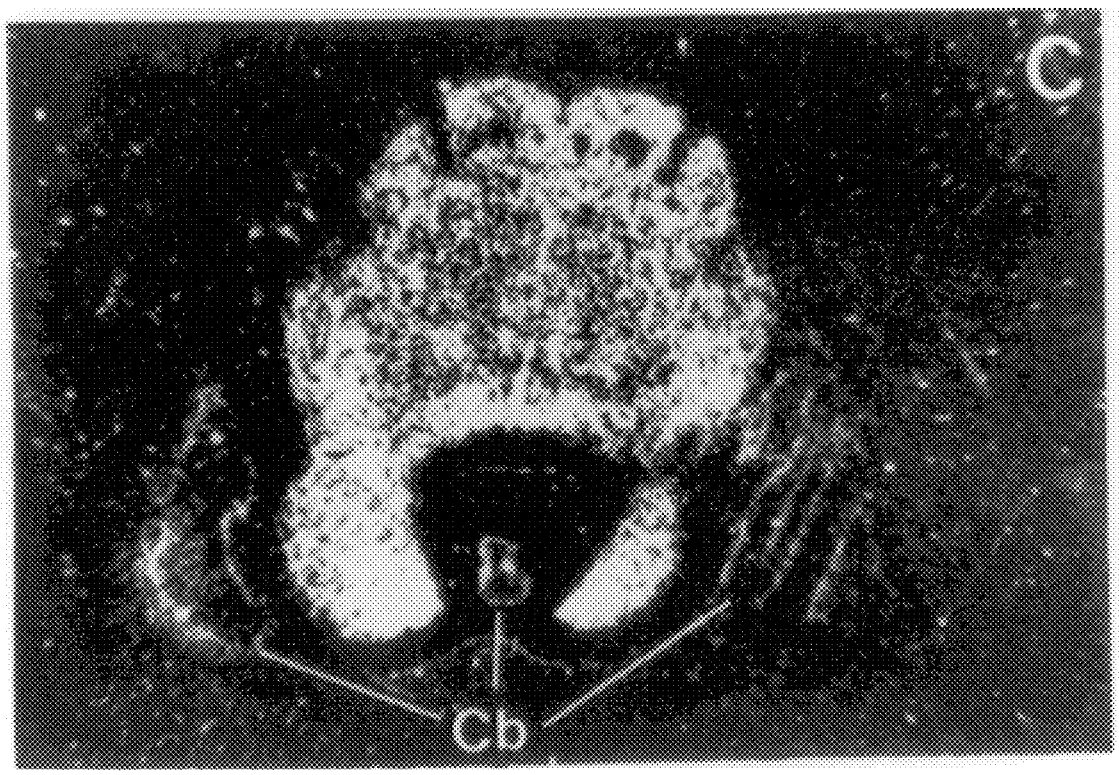
Figure 4A:
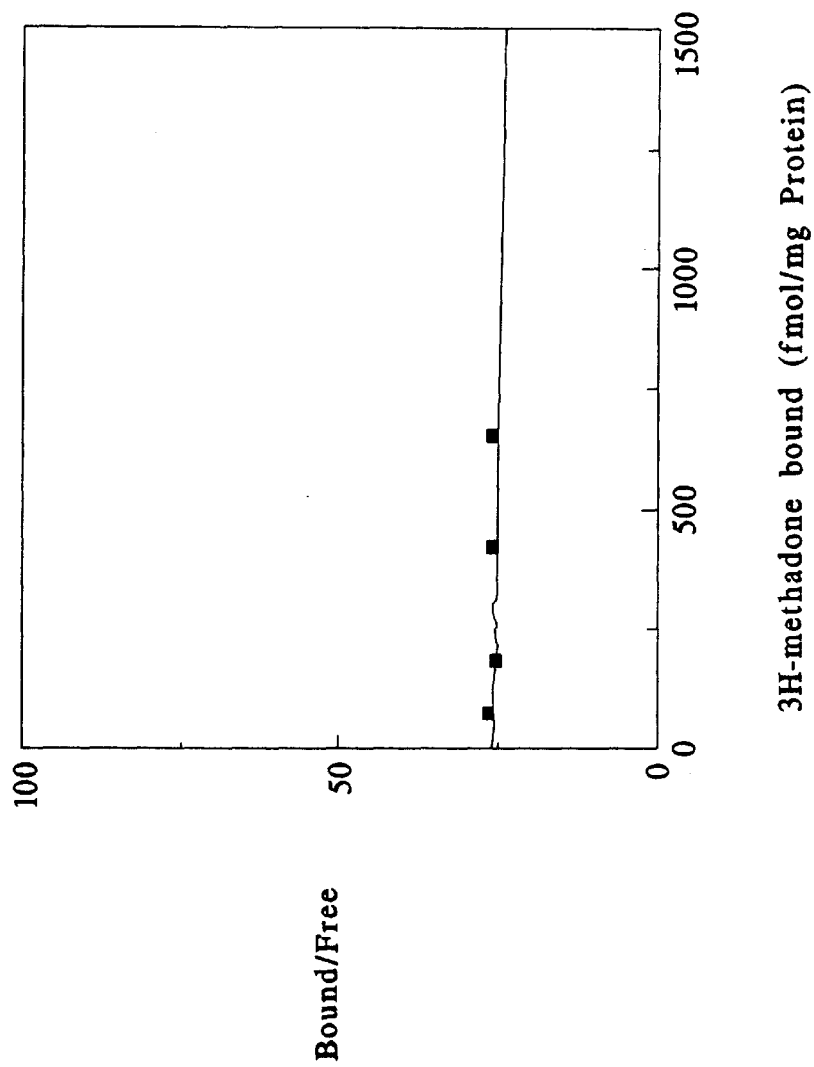
Figure 4B:
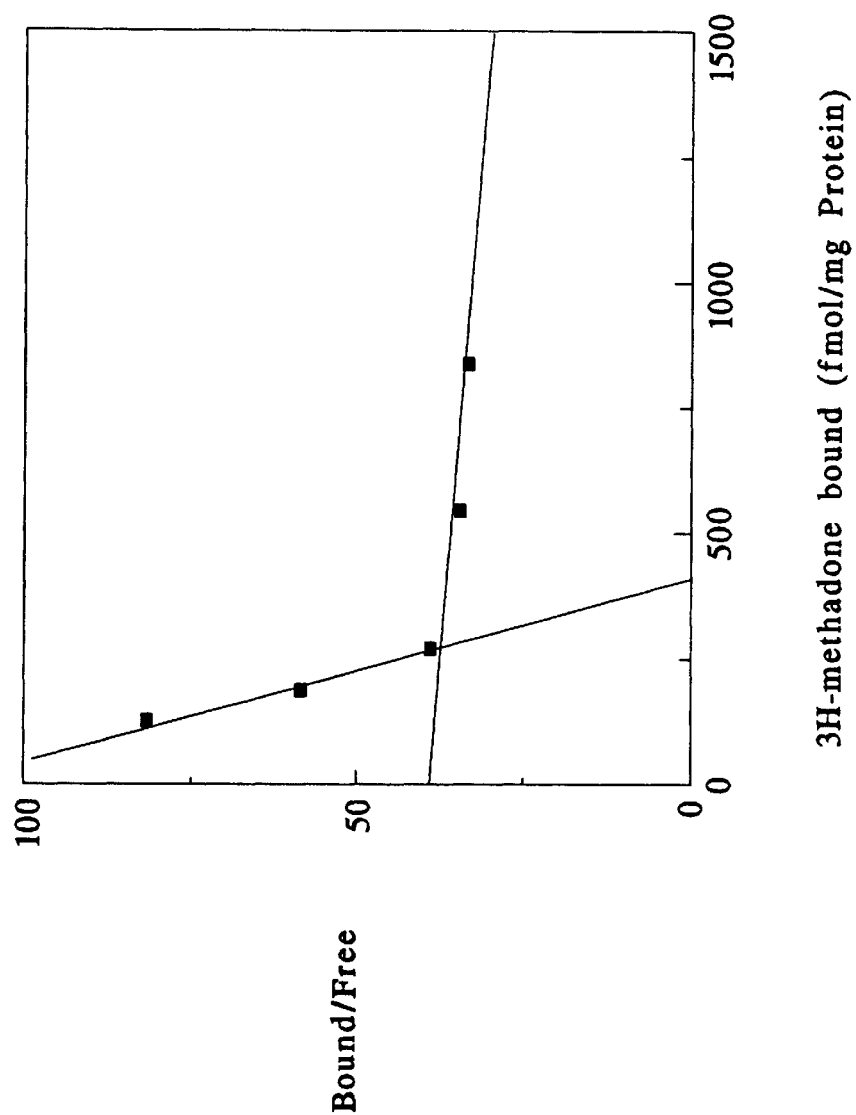

Results of these experiments are shown in FIGS. 3A through 3C. FIG. 3A shows a section through the frontal cortex, preoptic area and caudate putamen; FIG. 3B shows a section through the hypothalamus, thalamus and hippocampus; and FIG. 3C shows a section through the pons and cerebellum. These experiments localized high level MSOR expression in the hypothalamus (arcuate (Arc), posterior (PH), lateral (LH) and ventromedial (VMH) hypothalamic nuclei FIG. 3B), certain nuclei of the thalamus (paraventricular thalamic nuclei (PVP) FIG. 3B), the medial habenula (MHb, FIG. 3B), the CA regions of the hypothalamus, the dentate gyrus (DG, Panel B), the locus coeruleus and certain cortical areas (medial preoptic are (MPA) FIG. 3A and the cortex (Cx), Panel B). Virtually no signal was seen in the caudate putamen (Cpu FIG. 3A) or cerebellum (Cb, FIG. 3C). Strong hybridization was also detected in sections of the brainstem FIG. 3C and the spinal cord (not shown).

These results demonstrate that the MSOR receptor disclosed herein is expressed in rat brain in a variety of anatomically-distinct sites, suggesting an important role for this receptor in both higher brain function and central nervous system control of motor and sensory nerve signalling.

EXAMPLE 5

Construction of Vaccinia Virus-Recombinant Expression Constructs for Functional Expression of the MSOR Opioid Receptor Using an alternative approach, the MSOR opioid receptor protein of the invention is expressed in human HeLa (vulval adenocarcinoma) cells via a vaccinia virus-based construct. In these experiments, the MSOR receptor cDNA of the invention is excised from the RcRSV construct and subcloned into a modified pBluescript (Strategene) vector wherein the MSOR receptor cDNA is under the control of a bacteriophage T7 RNA polymerase promoter (as is described in Blakely et al., 1991, Anal. Biochem. 194: 302–308). HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with the MSOR receptor construct described above using a lipofectin-mediated (Bethesda Research Labs, Gaithersburg, Md.) transfection protocol (see Feigner et al., 1987, Proc. Nat. Acad. Sci. USA 84: 7413–7417). Cells are then incubated for 12–24 h before being assayed for MSOR receptor expression by functional assays or Northern hybridization assays.

EXAMPLE 6

Construction of Fusion Proteins-Recombinant Expression Constructs for Expression of Immunologically-Active Epitopes of the MSOR Opioid Receptor The MSOR opioid receptor protein of the invention are expressed as fusion proteins in bacteria to produce immunologically-active epitopes. In these experiments, the MSOR opioid receptor cDNA of the invention is excised from the RcRSV construct and subcloned into a pGEX-2T construct (Pharmacia, Piscataway, N.J.) whereby the coding sequences of the MSOR receptor cDNA is translationally in-frame with sequences encoding glutathione-S-transferase (described in Arriza et al., 1992, J. Neurosci. 12: 4045–4055), or any other protein construct for which a preparative isolation method is available. After introduction of the fusion construct into bacterial cells (*E. coli*, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against the MSOR opioid receptor of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual,* Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid encoding a mammalian methadone-specific opioid receptor wherein said nucleic acid hybridizes to a nucleic acid probe that is the complement to the sequence identified by Seq. I.D. No. 3 at a temperature of 37° C. in a solution of 5×SSC, 50% formamide, and 5×Denhardt's solution, wherein hybridization is detected after washing in a solution of 0.5×SSC/0.1% SDS at 55° C., and wherein the receptor has no specific binding to DAMGO, DPDPE, U-69,593, bremacozine, dihydromorphine, ethylketocyclazocine or beta-endorphin, and specifically binds methadone with a dissociation constant of about $10^{-10}$M.

2. A cell membrane preparation comprising a mammalian methadone-specific opioid receptor having an amino acid sequence identified by SEQ ID No.:4, wherein said membrane preparation is produced by a cell that has been transfected with a recombinant expression vector comprising a nucleic acid encoding the receptor, wherein said cell does not express an endogenous methadone-specified opioid receptor.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ATGAATTCAC NRTSATGAGY GTSGACHGHT A      31

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TTGTCGACRT ARRAGRAYNG GRTT      24

(2) INFORMATION FOR SEQ ID NO:3:

(i) SEQUENCE CHARACTERISTICS:
      (A) LENGTH: 1452 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: 5'UTR
      (B) LOCATION: 1..181

(ix) FEATURE:
      (A) NAME/KEY: CDS
      (B) LOCATION: 182..1282

(ix) FEATURE:
      (A) NAME/KEY: 3'UTR
      (B) LOCATION: 1283..1452

(xi) SEQUENCE DESCRIPTION: SEQ ID NO:3:

```
CCGAGGAGCC ATTCCCAGCC GCAGCAGACC CCAATCTAGA GTGAGAGTCA TTGCTCAGTC      60

CACTGTGCTC CTGCCTGCCC GCCTTTCTGC TAAGCATTGG GGTCTATTTT GCGCCCAGCT     120

TCTGAAGAGG CTGTGTGTGC CGTTGGAGGA ACTGTACTGA GTGGCTTTGC AGGGTGACAG     180
```

| | | | | | | | | | | | | | | | | |
|---|---|---|---|---|---|---|---|---|---|---|---|---|---|---|---|---|
| C ATG | GAG | TCC | CTC | TTT | CCT | GCT | CCA | TAC | TGG | GAG | GTC | TTG | CAT | GGC | | 226 |
| Met | Glu | Ser | Leu | Phe | Pro | Ala | Pro | Tyr | Trp | Glu | Val | Leu | His | Gly | | |
| 1 | | | 5 | | | | | 10 | | | | | 15 | | | |

| AGC | CAC | TTT | CAA | GGG | AAC | CTG | TCC | CTC | CTA | AAT | GAG | ACC | GTA | CCC | CAC | 274 |
|---|---|---|---|---|---|---|---|---|---|---|---|---|---|---|---|---|
| Ser | His | Phe | Gln | Gly | Asn | Leu | Ser | Leu | Leu | Asn | Glu | Thr | Val | Pro | His | |
| | | | 20 | | | | | 25 | | | | | 30 | | | |

| CAC | CTG | CTC | CTC | AAT | GCT | AGT | CAC | AGC | GCC | TTC | CTG | CCC | CTT | GGA | CTC | 322 |
|---|---|---|---|---|---|---|---|---|---|---|---|---|---|---|---|---|
| His | Leu | Leu | Leu | Asn | Ala | Ser | His | Ser | Ala | Phe | Leu | Pro | Leu | Gly | Leu | |
| | | | 35 | | | | | 40 | | | | | 45 | | | |

| AAG | GTC | ACC | ATC | GTG | GGG | CTC | ATC | TTG | GCT | GTG | TGC | ATC | GGG | GGG | CTC | 370 |
|---|---|---|---|---|---|---|---|---|---|---|---|---|---|---|---|---|
| Lys | Val | Thr | Ile | Val | Gly | Leu | Ile | Leu | Ala | Val | Cys | Ile | Gly | Gly | Leu | |
| | | | 50 | | | | | 55 | | | | | 60 | | | |

| CTG | GGG | AAC | TGC | CTC | GTC | ATG | TAT | GTC | ATC | CTC | AGG | ACA | CCC | AAG | ATG | 418 |
|---|---|---|---|---|---|---|---|---|---|---|---|---|---|---|---|---|
| Leu | Gly | Asn | Cys | Leu | Val | Met | Tyr | Val | Ile | Leu | Arg | Thr | Pro | Lys | Met | |
| 65 | | | | | 70 | | | | | 75 | | | | | | |

| AAG | ACA | GCT | ACC | AAC | ATT | TAC | ATA | TTT | AAT | CTG | GCA | CTG | GCT | GAT | ACC | 466 |
|---|---|---|---|---|---|---|---|---|---|---|---|---|---|---|---|---|
| Lys | Thr | Ala | Thr | Asn | Ile | Tyr | Ile | Phe | Asn | Leu | Ala | Leu | Ala | Asp | Thr | |
| 80 | | | | | 85 | | | | | 90 | | | | | 95 | |

| CTG | GTC | TTG | CTA | ACA | CTG | CCC | TTC | CAG | GGC | ACA | GAC | ATC | CTA | CTG | GGC | 514 |
|---|---|---|---|---|---|---|---|---|---|---|---|---|---|---|---|---|
| Leu | Val | Leu | Leu | Thr | Leu | Pro | Phe | Gln | Gly | Thr | Asp | Ile | Leu | Leu | Gly | |
| | | | 100 | | | | | 105 | | | | | 110 | | | |

| TTC | TGG | CCA | TTT | GGG | AAA | GCA | CTC | TGC | AAG | ACT | GTC | ATT | GCT | ATC | GAC | 562 |
|---|---|---|---|---|---|---|---|---|---|---|---|---|---|---|---|---|
| Phe | Trp | Pro | Phe | Gly | Lys | Ala | Leu | Cys | Lys | Thr | Val | Ile | Ala | Ile | Asp | |
| | | | 115 | | | | | 120 | | | | | 125 | | | |

| TAC | TAC | AAC | ATG | TTT | ACC | AGC | ACT | TTT | ACT | CTG | ACC | GCC | ATG | AGC | GTA | 610 |
|---|---|---|---|---|---|---|---|---|---|---|---|---|---|---|---|---|
| Tyr | Tyr | Asn | Met | Phe | Thr | Ser | Thr | Phe | Thr | Leu | Thr | Ala | Met | Ser | Val | |
| | | | 130 | | | | | 135 | | | | | 140 | | | |

| GAC | CGC | TAT | GTG | GCT | ATC | TGC | CAC | CCT | ATC | CGT | GCC | CTT | GAT | GTT | CGG | 658 |
|---|---|---|---|---|---|---|---|---|---|---|---|---|---|---|---|---|
| Asp | Arg | Tyr | Val | Ala | Ile | Cys | His | Pro | Ile | Arg | Ala | Leu | Asp | Val | Arg | |
| | | 145 | | | | | 150 | | | | | 155 | | | | |

| ACA | TCC | AGC | AAA | GCC | CAG | GCT | GTT | AAT | GTG | GCC | ATA | TGG | GCC | CTG | GCT | 706 |
|---|---|---|---|---|---|---|---|---|---|---|---|---|---|---|---|---|
| Thr | Ser | Ser | Lys | Ala | Gln | Ala | Val | Asn | Val | Ala | Ile | Trp | Ala | Leu | Ala | |
| 160 | | | | | 165 | | | | | 170 | | | | | 175 | |

| TCA | GTG | GTT | GGT | GTT | CCT | GTT | GCC | ATC | ATG | GGT | TCA | GCA | CAA | GTG | GAA | 754 |
|---|---|---|---|---|---|---|---|---|---|---|---|---|---|---|---|---|
| Ser | Val | Val | Gly | Val | Pro | Val | Ala | Ile | Met | Gly | Ser | Ala | Gln | Val | Glu | |
| | | | 180 | | | | | 185 | | | | | 190 | | | |

| GAT | GAA | GAG | ATC | GAG | TGC | CTG | GTG | GAG | ATC | CCT | GCC | CCT | CAG | GAC | TAT | 802 |
|---|---|---|---|---|---|---|---|---|---|---|---|---|---|---|---|---|
| Asp | Glu | Glu | Ile | Glu | Cys | Leu | Val | Glu | Ile | Pro | Ala | Pro | Gln | Asp | Tyr | |
| | | | 195 | | | | | 200 | | | | | 205 | | | |

| TGG | GGC | CCT | GTA | TTC | GCC | ATC | TGC | ATC | TTC | CTT | TTT | TCC | TTC | ATC | ATC | 850 |
|---|---|---|---|---|---|---|---|---|---|---|---|---|---|---|---|---|
| Trp | Gly | Pro | Val | Phe | Ala | Ile | Cys | Ile | Phe | Leu | Phe | Ser | Phe | Ile | Ile | |
| | | | 210 | | | | | 215 | | | | | 220 | | | |

| CCT | GTG | CTG | ATC | ATC | TCT | GTC | TGC | TAC | AGC | CTC | ATG | ATT | CGA | CGA | CTT | 898 |
|---|---|---|---|---|---|---|---|---|---|---|---|---|---|---|---|---|
| Pro | Val | Leu | Ile | Ile | Ser | Val | Cys | Tyr | Ser | Leu | Met | Ile | Arg | Arg | Leu | |
| | | 225 | | | | | 230 | | | | | 235 | | | | |

| CGT | GGT | GTC | CGT | CTG | CTT | TCA | GGC | TCC | CGG | GAG | AAG | GAC | CGA | AAC | CTG | 946 |
|---|---|---|---|---|---|---|---|---|---|---|---|---|---|---|---|---|
| Arg | Gly | Val | Arg | Leu | Leu | Ser | Gly | Ser | Arg | Glu | Lys | Asp | Arg | Asn | Leu | |
| 240 | | | | | 245 | | | | | 250 | | | | | 255 | |

| CGG | CGT | ATC | ACT | CGA | CTG | GTG | CTG | GTA | GTG | GTG | GCT | GTG | TTT | GTG | GGC | 994 |
|---|---|---|---|---|---|---|---|---|---|---|---|---|---|---|---|---|
| Arg | Arg | Ile | Thr | Arg | Leu | Val | Leu | Val | Val | Val | Ala | Val | Phe | Val | Gly | |
| | | | 260 | | | | | 265 | | | | | 270 | | | |

| TGC | TGG | ACG | CCT | GTG | CAG | GTG | TTT | GTC | CTG | GTT | CAA | GGA | CTG | GGT | GTT | 1042 |
|---|---|---|---|---|---|---|---|---|---|---|---|---|---|---|---|---|
| Cys | Trp | Thr | Pro | Val | Gln | Val | Phe | Val | Leu | Val | Gln | Gly | Leu | Gly | Val | |

```
                275                 280                 285
CAG CCA GGT AGT GAG ACT GCA GTT GCC ATC CTG CGC TTC TGC ACA GCC    1090
Gln Pro Gly Ser Glu Thr Ala Val Ala Ile Leu Arg Phe Cys Thr Ala
        290                 295                 300

CTG GGC TAT GTC AAC AGT TGT CTC AAT CCC ATT CTC TAT GCT TTC CTG    1138
Leu Gly Tyr Val Asn Ser Cys Leu Asn Pro Ile Leu Tyr Ala Phe Leu
    305                 310                 315

GAT GAG AAC TTC AAG GCC TGC TTT AGA AAG TTC TGC TGT GCT TCA TCC    1186
Asp Glu Asn Phe Lys Ala Cys Phe Arg Lys Phe Cys Cys Ala Ser Ser
320                 325                 330                 335

CTG CAC CGG GAG ATG CAG GTT TCT GAT CGT GTG CGG ACG ATT GCC AAG    1234
Leu His Arg Glu Met Gln Val Ser Asp Arg Val Arg Thr Ile Ala Lys
            340                 345                 350

GAT GTT GGC CTT GGT TGC AAG ACT TCT GAG ACA GTA CCA CGG CCA GCA    1282
Asp Val Gly Leu Gly Cys Lys Thr Ser Glu Thr Val Pro Arg Pro Ala
                355                 360                 365

TGACTAGGCG TGGACCTGCC CATGGTGCCT GTCAGCCCAC AGAGCCCATC CTACACCCAA  1342

CACGGAGCTC ACACAGGTCA CTGCTCTCTA GGTTGACCCT GAACCTTGAG CATCTGGAGC  1402

CTTGAATGGC TTTTCTTTTG GATCAGGATG CTCAGTCCTA GAGGAAGACC             1452

(2) INFORMATION FOR SEQ ID NO:4:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Ser Leu Phe Pro Ala Pro Tyr Trp Glu Val Leu His Gly Ser
 1               5                  10                  15

His Phe Gln Gly Asn Leu Ser Leu Leu Asn Glu Thr Val Pro His His
                20                  25                  30

Leu Leu Leu Asn Ala Ser His Ser Ala Phe Leu Pro Leu Gly Leu Lys
        35                  40                  45

Val Thr Ile Val Gly Leu Ile Leu Ala Val Cys Ile Gly Gly Leu Leu
    50                  55                  60

Gly Asn Cys Leu Val Met Tyr Val Ile Leu Arg Thr Pro Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Lys Ala Leu Cys Lys Thr Val Ile Ala Ile Asp Tyr
        115                 120                 125

Tyr Asn Met Phe Thr Ser Thr Phe Thr Leu Thr Ala Met Ser Val Asp
    130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
            180                 185                 190

Glu Glu Ile Glu Cys Leu Val Glu Ile Pro Ala Pro Gln Asp Tyr Trp
        195                 200                 205
```

```
Gly Pro Val Phe Ala Ile Cys Ile Phe Leu Phe Ser Phe Ile Ile Pro
    210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
            260                 265                 270

Trp Thr Pro Val Gln Val Phe Val Leu Val Gln Gly Leu Gly Val Gln
            275                 280                 285

Pro Gly Ser Glu Thr Ala Val Ala Ile Leu Arg Phe Cys Thr Ala Leu
        290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ser Leu
                325                 330                 335

His Arg Glu Met Gln Val Ser Asp Arg Val Arg Thr Ile Ala Lys Asp
            340                 345                 350

Val Gly Leu Gly Cys Lys Thr Ser Glu Thr Val Pro Arg Pro Ala
            355                 360                 365
```

(2) INFORMATION FOR SEQ ID NO:5:

(i) SEQUENCE CHARACTERISTICS:
        (A) LENGTH: 398 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..398
        (D) OTHER INFORMATION: /label= Identifier
           /note= "Rat Mu-Opioid Receptor"

(xi) SEQUENCE DESCRIPTION: SEQ ID NO:5:

```
Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
```

```
                        165                 170                 175
Asp Phe Arg Thr Pro Arg Asn Ala Lys Ile Val Asn Val Cys Asn Trp
                180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
        210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Lys Ala
        290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
                340                 345                 350

Pro Thr Ser Ser Thr Ile Glu Gln Gln Asn Ser Thr Arg Val Arg Gln
                355                 360                 365

Asn Thr Arg Glu His Pro Ser Thr Ala Asn Thr Val Asp Arg Thr Asn
            370                 375                 380

His Gln Leu Glu Asn Leu Glu Ala Glu Thr Ala Pro Leu Pro
385                 390                 395

(2) INFORMATION FOR SEQ ID NO:6:

(i) SEQUENCE CHARACTERISTICS:
        (A) LENGTH: 372 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..372
        (D) OTHER INFORMATION: /label= Identifier
            /note= "Mouse Delta-Opioid Receptor"

(xi) SEQUENCE DESCRIPTION: SEQ ID NO:6:

Met Glu Leu Val Pro Ser Ala Arg Ala Glu Leu Gln Ser Ser Pro Leu
1               5                   10                  15

Val Asn Leu Ser Asp Ala Phe Pro Ser Ala Phe Pro Ser Ala Gly Ala
                20                  25                  30

Asn Ala Ser Gly Ser Pro Gly Ala Arg Ser Ala Ser Ser Leu Ala Leu
            35                  40                  45

Ala Ile Ala Ile Thr Ala Leu Tyr Ser Ala Val Cys Ala Val Gly Leu
        50                  55                  60

Ile Gly Asn Val Leu Val Met Leu Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95
```

-continued

```
Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
            115                 120                 125

Tyr Tyr Asn Met Phe Thr Ser Ile Phe Thr Leu Thr Met Met Ser Val
130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
            165                 170                 175

Ser Gly Val Gly Val Pro Ile Met Val Met Ala Val Thr Gln Pro Arg
            180                 185                 190

Asp Phe Ala Val Val Cys Met Leu Gln Phe Pro Ser Pro Ser Trp Tyr
            195                 200                 205

Trp Asp Thr Val Thr Lys Ile Cys Val Phe Ile Phe Ala Phe Val Val
            210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
            245                 250                 255

Arg Arg Ile Thr Arg Met Val Leu Val Val Val Gly Ala Phe Val Val
            260                 265                 270

Cys Trp Ala Pro Ile His Ile Phe Val Ile Val Trp Thr Leu Val Asp
            275                 280                 285

Ile Asn Arg Arg Asp Pro Leu Val Val Ala Ala Leu His Leu Cys Ile
290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
            325                 330                 335

Cys Gly Arg Gln Glu Pro Gly Ser Leu Arg Arg Pro Arg Gln Ala Thr
            340                 345                 350

Thr Arg Glu Arg Val Thr Ala Cys Thr Pro Ser Asp Gly Pro Gly Gly
            355                 360                 365

Gly Ala Ala Ala
    370
```

(2) INFORMATION FOR SEQ ID NO:7:

(i) SEQUENCE CHARACTERISTICS:
        (A) LENGTH: 380 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..380
        (D) OTHER INFORMATION: /label= Identifier
            /note= "Mouse Kappa-Opioid Receptor"

(xi) SEQUENCE DESCRIPTION: SEQ ID NO:7:

```
Met Glu Ser Pro Ile Gln Ile Phe Arg Gly Asp Pro Gly Pro Thr Cys
1               5                   10                  15

Ser Pro Ser Ala Cys Leu Leu Pro Asn Ser Ser Ser Trp Phe Pro Asn
            20                  25                  30
```

```
Trp Ala Glu Ser Asp Ser Asn Gly Ser Val Gly Ser Glu Asp Gln Gln
            35                  40                  45

Leu Glu Ser Ala His Ile Ser Pro Ala Ile Pro Val Ile Ile Thr Ala
        50                  55                  60

Val Tyr Ser Val Val Phe Val Val Gly Leu Val Gly Asn Ser Leu Val
65                      70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
               100                 105                 110

Pro Phe Gln Ser Ala Val Tyr Leu Met Asn Ser Trp Pro Phe Gly Asp
           115                 120                 125

Val Leu Cys Lys Ile Val Ile Ser Ile Asp Tyr Tyr Asn Met Phe Thr
       130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
               165                 170                 175

Ile Ile Asn Ile Cys Ile Trp Leu Leu Ala Ser Ser Val Gly Ile Ser
               180                 185                 190

Ala Ile Val Leu Gly Gly Thr Lys Val Arg Glu Asp Val Asp Val Ile
       195                 200                 205

Glu Cys Ser Leu Gln Phe Pro Asp Asp Glu Tyr Ser Trp Trp Asp Leu
       210                 215                 220

Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
               245                 250                 255

Arg Leu Leu Ser Gly Ser Arg Glu Lys Asp Arg Asn Leu Arg Arg Ile
           260                 265                 270

Thr Lys Leu Val Leu Val Val Ala Val Phe Ile Ile Cys Trp Thr
       275                 280                 285

Pro Ile His Ile Phe Ile Leu Val Glu Ala Leu Gly Ser Thr Ser His
       290                 295                 300

Ser Thr Ala Ala Leu Ser Ser Tyr Tyr Phe Cys Ala Ile Leu Gly Tyr
305                 310                 315                 320

Thr Asn Ser Ser Leu Asn Pro Val Leu Tyr Ala Phe Leu Asp Glu Asn
           325                 330                 335

Phe Lys Arg Cys Phe Arg Asp Phe Cys Phe Pro Ile Lys Met Arg Met
           340                 345                 350

Glu Arg Gln Ser Thr Asn Arg Val Arg Asn Thr Val Gln Asp Pro Ala
       355                 360                 365

Ser Met Arg Asp Val Gly Gly Met Asn Lys Pro Val
370                 375                 380
```